United States Patent [19]

Mikulicz et al.

[11] 4,220,806
[45] Sep. 2, 1980

[54] PLURAL STAGES OF HYDROFLUORIC ACID ALKYLATION UTILIZING SEPARATED ACID PHASE AS CATALYST IN THE SUBSEQUENT STAGE

[75] Inventors: Michael Z. Mikulicz, Palatine; James F. Himes, Mt. Prospect, both of Ill.

[73] Assignee: UOP Inc., Des Plaines, Ill.

[21] Appl. No.: 32,611

[22] Filed: Apr. 23, 1979

[51] Int. Cl.² ............................................. C07C 3/54
[52] U.S. Cl. .................................. 585/716; 585/723
[58] Field of Search ................................ 585/716, 723

[56] References Cited

U.S. PATENT DOCUMENTS

| | | | |
|---|---|---|---|
| 3,246,047 | 4/1966 | Chapman et al. | 585/723 |
| 3,911,043 | 10/1975 | Anderson | 585/723 |
| 4,046,516 | 9/1977 | Burton et al. | 585/716 |

*Primary Examiner*—George Crasanakis
*Attorney, Agent, or Firm*—James R. Hoatson, Jr.; Robert W. Welch; William H. Page, II

[57] ABSTRACT

A process is disclosed for the alkylation of an isoparaffinic hydrocarbon with an olefin-acting alkylating agent. The isoparaffinic hydrocarbon is commingled with a first portion of said alkylating agent in a first alkylation reaction zone at alkylation reaction conditions in contact with a hydrofluoric acid catalyst. The acid phase of the effluent from the first alkylation reaction zone is separated, and the hydrocarbon phase, comprising alkylate and unreacted isoparaffin, is commingled with a second portion of said alkylating agent at alkylation reaction conditions in a second alkylation reaction zone in contact with a hydrofluoric acid catalyst separately charged thereto, the hydrofluoric acid catalyst being that separated from the effluent of the first alkylation reaction zone. The acid phase is separated from the effluent from the second alkylation reaction zone and recycled to the first alkylation reaction zone, and the alkylate product is recovered from the hydrocarbon phase.

7 Claims, 1 Drawing Figure

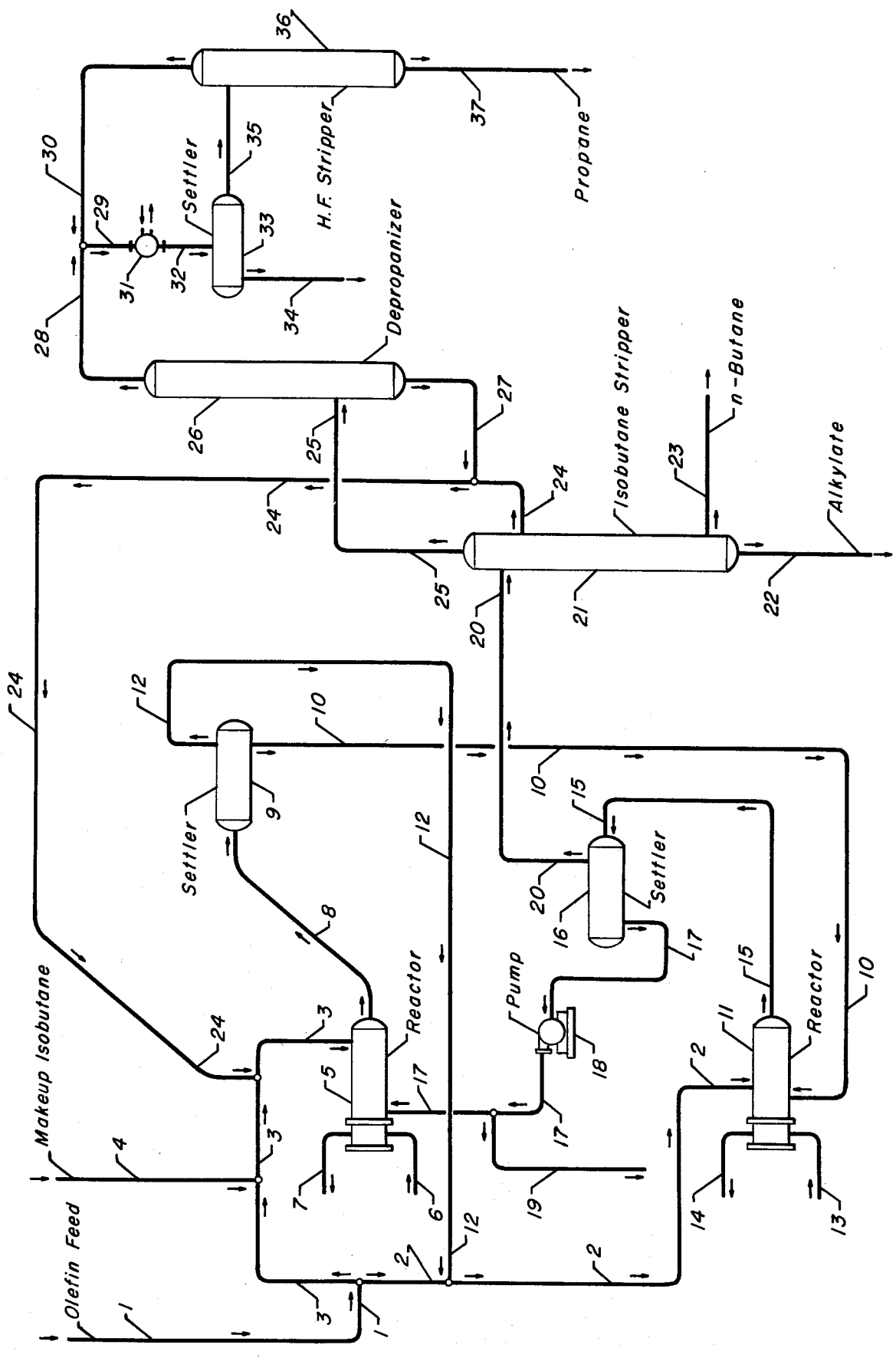

PLURAL STAGES OF HYDROFLUORIC ACID ALKYLATION UTILIZING SEPARATED ACID PHASE AS CATALYST IN THE SUBSEQUENT STAGE

This invention relates to the alkylation of an isoparaffinic hydrocarbon with an olefin-acting alkylating agent. More specifically, this invention relates to the hydrofluoric acid-catalyzed alkylation of an isoparaffinic hydrocarbon with an olefin-acting alkylating agent to provide valuable motor fuel components. The alkylation of isoparaffinic hydrocarbons such as isobutane, isopentane, and the like, with olefin-acting alkylating agents, including olefinic hydrocarbons such as propylene, butylenes and amylenes, and also alkyl halides and the like, is a well known and commercially important process for the production of gasoline boiling range hydrocarbons. The $C_5$–$C_{10}$ hydrocarbons generally produced by the alkylation reaction are known collectively as alkylate. The alkylate is especially valuable as a motor fuel blending stock because of its high motor and research octane ratings. The alkylate is generally utilized to improve the overall octane ratings of lower quality gasoline stocks to comply with the octane requirements of modern automobile engines. High octane alkylate components are particularly important to a motor fuel in the absence of alkyl lead additives and, as said additives are phased out, there is a continuing effort to provide higher quality alkylate products.

In general, commercial processes for the alkylation of an isoparaffinic hydrocarbon with an olefin-acting alkylation agent employ isobutane, and sometimes isopentane, as the isoparaffinic hydrocarbon, and the olefin-acting alkylating agent is typically propylene, butylenes, amylenes, or mixtures thereof. Catalysts include hydrofluoric acid, sulfuric acid, and other acid or acid-acting catalysts such as anhydrous aluminum chloride. In a hydrofluoric acid-catalyzed alkylation process, the isoparaffinic hydrocarbon, olefin-acting alkylating agent and hydrofluoric acid catalyst are admixed in an alkylation reactor and, after the reaction is substantially complete, the reaction mixture is recovered and allowed to settle into an acid phase and an immiscible hydrocarbon phase. The acid phase is separated and recycled to the alkylation reactor, and the hydrocarbon phase is further processed for the recovery of the alkylate product, and for the recovery of unreacted isoparaffinic hydrocarbon for recycle to the alkylation reactor to furnish a major portion of the isoparaffinic hydrocarbon reactant therein.

In order to produce an acceptable yield of high quality alkylate in a commercial isoparaffin-olefin alkylation process, it has been found necessary to conduct the alkylation reaction at fairly specific alkylation reaction conditions, such as temperature and pressure, and the concentration of both the catalyst and the reactants is of considerable importance. For example, to provide a product of desired utility as a high octane blending material, a substantial excess of isoparaffinic hydrocarbon is required relative to the amount of olefin-acting alkylating agent contained in the alkylation reaction mixture to provide, e.g., an isoparaffin/olefin mole ratio of from about 8:1 to about 30:1. The quality of the alkylate is known to improve as the isoparaffin/olefin mole ratio is increased. The primary limitations on said increase are the capital and utilities cost of the equipment required to process the excess isoparaffin. It will be appreciated that the larger the volume of excess isoparaffin which must be processed through the various vessels which constitute a commercial alkylation process, the larger the required capacity of said vessels, particularly the fractionation equipment required for an adequate separation of the alkylate from the excess isoparaffin. In a commercial process, the quality of the alkylate is thus limited by the amount of unreacted isoparaffin which can be economically processed and separated from the alkylate for recycle to the alkylation reactor. The expense and difficulty of providing a large isoparaffin throughput, fractionation and recycle in order to produce alkylate of adequate quality may be obviated, in part, through the practice of the process of this invention.

It is an object of this invention to provide a process for alkylating an isoparaffin with an olefin-acting alkylating agent to produce an alkylation reaction product possessing superior qualities as a motor fuel component.

It is a further object of this invention to provide a process for alkylating an isoparaffinic hydrocarbon with an olefin-acting alkylating agent wherein a smaller scale of isoparaffinic hydrocarbon fractionation and recycle is required in order to obtain a high quality motor fuel alkylate product.

In one of its broad aspects, the present invention embodies a process for the alkylation of an isoparaffinic hydrocarbon with an olefin-acting alkylating agent which comprises commingling said isoparaffinic hydrocarbon and a first portion of said olefin-acting alkylating agent at alkylation reaction conditions in a first alkylation reaction zone in contact with a hydrofluoric acid catalyst separately charged thereto; separating the acid phase of the effluent from said first alkylation reaction zone and recovering a hydrocarbon phase comprising alkylate and unreacted isoparaffinic hydrocarbon; commingling said hydrocarbon phase with a second portion of said olefin-acting alkylating agent at alkylation reaction conditions in a second alkylation reaction zone in contact with a hydrofluoric acid catalyst separately charged thereto, said hydrofluoric acid catalyst being that previously separated from the effluent of said first alkylation reaction zone; separating the acid phase of the effluent from said second alkylation reaction zone, and recycling said acid phase to said first alkylation reaction zone; and recovering the alkylate product from the hydrocarbon phase.

Other objects, embodiments and advantages of the present invention will become apparent from the following detailed specification.

Closely related prior art is depicted in U.S. Pat. No. 3,846,505 which concerns an alkylation process, the practice of which affords a substantial reduction in the amount of the isoparaffinic hydrocarbon reactant required to provide a desired molar excess with respect to a given amount of olefin-acting alkylating agents. By passing only a portion of the alkylating agent to a first alkylation reactor, a significantly smaller amount of isoparaffinic hydrocarbon is required in the overall alkylation process. Thus, the hydrocarbon effluent from the first alkylation reactor, comprising unreacted isoparaffinic hydrocarbon is separated and charged to a second alkylation reactor, and said isoparaffinic hydrocarbon is contacted therein with the remaining portion of the alkylating agent at alkylation reaction conditions. In this manner, although the amount of isoparaffinic hydrocarbon required for the overall alkylation process is substantially reduced, there is provided a desired molar excess of said hydrocarbon to each of the alkylation reactors.

The following is in illustration of an alkylation process representing one preferred embodiment of the present invention. The embodiment is illustrated with reference to the attached schematic drawing and, for purposes of illustration, the isoparaffinic hydrocarbon is isobutane and the olefin-acting alkylating agent is a mixture of propylene and butylenes. It is not intended that the schematic drawing, nor the various reactants described with reference thereto, shall serve as an undue limitation on the generally broad scope of the invention as set out on the appended claims.

Referring then to the drawing, an olefinic hydrocarbon feedstock is charged to the alkylation process by way of line 1. The olefinic hydrocarbon feedstock contains equimolar amounts of propylene and butylenes and is charged to the process at a rate to provide about 300 moles of propylene and 300 moles of mixed butylenes per hour. Other hydrocarbons typically present in a commercial olefinic hydrocarbon feedstock, but not essential to the alkylation process, include isobutane, n-butane and propane, and these hydrocarbons are charged to the alkylation process illustrated at an hourly rate of about 120, 35 and 70 moles, respectively. In any case, the olefinic hydrocarbon feedstock is equally divided into lines 2 and 3, each of said lines thus containing a flow of 150 moles of propylene, 150 moles of mixed butylenes, 60 moles of isobutane, 17.5 moles of n-butane and 35 moles of propane per hour. Make-up isobutane is charged to the alkylation process via line 4 to be admixed with that portion of the olefinic hydrocarbon feedstock diverted through line 3. The make-up isobutane is charged at a rate of about 500 moles per hour together with about 50 moles of n-butane and 10 moles of propane per hour as non-reactive contaminants commonly contained in available isobutane feedstocks.

The hydrocarbon reactant mixture is continued through line 3 together with recycled isobutane from line 24 and charged to a first alkylation reactor 5. The recycled isobutane from line 24 is supplied at a rate of about 3,550 moles per hour, and said recycled isobutane will typically further contain about 525 moles of n-butane and 225 moles of propane per hour as products of imprecise fractionation. The total hydrocarbon charge to the alkylation reactor 5 will thus include about 150 moles of propylene, 150 moles of mixed butylenes and 4,110 moles of isobutane per hour, and will further contain as non-reactive hydrocarbons about 270 moles of propane and 557.5 moles of n-butane per hour. The isobutane will therefore be charged to the alkylation reactor 5 in about a 13.7:1 mole ratio with the olefinic hydrocarbons charged thereto. The combined feed is charged to the alkylation reactor 5 and admixed with the hydrofluoric acid alkylation catalyst to form an alkylation reaction mixture therein having an acid/hydrocarbon volume ratio of from about 1 to about 2. The hydrofluoric acid alkylation catalyst is charged to the alkylation reactor 5 from line 17 and comprises about 85 wt.% acid and less than about 1 wt.% water. The remainder comprises organic matter common to said alkylation catalyst. Alkylation reaction conditions in the first alkylation reactor 5 include a temperature of from about 90° to about 100° F. and a pressure sufficient to maintain substantially liquid phase reaction conditions. Cooling water is charged through line 6 and travels through the alkylation reactor 5 in indirect heat exchange relationship with the alkylation mixture contained therein. The cooling water is discharged through line 7. After a contact time of from about 0.1 to about 5 minutes, the alkylation reaction mixture is withdrawn from the first alkylation reactor 5 and transferred through line 8 to a settler 9. The reaction mixture is allowed to stand in the settler 9 and separate into an upper hydrocarbon phase and a lower hydrofluoric acid phase. The hydrofluoric acid is withdrawn from the bottom of settler 9 and routed to a second alkylation reactor 11 by way of line 10.

Referring back to the settler 9, the upper hydrocarbon phase recovered therein, representing the total hydrocarbon effluent from the first alkylation reactor 5, is withdrawn overhead through line 12 and is continued through line 12 to provide about 3,800 moles of isobutane, 557 moles of n-butane, 280 moles of propane and 300 moles of alkylate per hour to be commingled with that portion of the olefinic hydrocarbon feedstock previously diverted through line 2 from line 1. The combined hydrocarbon streams will thus afford a flow of 3,860 moles of isobutane, 150 moles of propylene, 150 moles of mixed butylenes, 575 moles of n-butane, 315 moles of propane and 300 moles of alkylate per hour, and this combined hydrocarbon stream is continued through line 2 and constitutes the total hydrocarbon charge to the second alkylation reactor 11. The isobutane/olefin mole ratio in said second alkylation reactor 11 will thus be about 13. The alkylation reaction conditions employed in the second alkylation reactor 11 are substantially as described with respect to alkylation reactor 5, except that a pressure differential of about 15 psig. is maintained to facilitate the transfer of the hydrofluoric acid catalyst to the second alkylation reactor 11, as well as the transfer of the hydrocarbon effluent from the settler 9. The heretofore mentioned hydrofluoric acid from line 10 is charged to the second alkylation reactor 11 and intimately admixed with the hydrocarbon feed from line 2 to form an alkylation reaction mixture therein. Cooling water, charged through line 13, is passed in indirect heat exchange relationship with the alkylation reaction mixture contained in the alkylation reactor 11, and the water is then discharged through line 14. The alkylation reaction mixture is withdrawn from the alkylation reactor 11 after a contact time of from about 0.1 to about 5 minutes and passed to a settler 16 by way of line 15. The reaction mixture is retained in the settler 16 free of agitation to facilitate separation of the immiscible hydrocarbon and acid phases therein. The hydrofluoric acid catalyst which settles out as the lower liquid phase is recovered from the bottom of the settler 16 through line 17 and recycled by means of pump 18 to a first alkylation reactor 5 for further use therein. It is contemplated that the hydrofluoric acid catalyst will require regeneration, in whole or in part, with continued use. This can be effected by taking a slip stream from line 17 and withdrawing the slip stream through line 19 for transfer to conventional regeneration means. The regeneration means, being conventional regeneration means and not essential to an understanding of the present invention, is not shown.

In any case, the hydrocarbon phase recovered in settler 16 is withdrawn overhead through line 20 and transferred to an isobutane stripper 21. About 325 moles of propane, 3,550 moles of isobutane, 575 moles of n-butane and 600 moles of alkylate are transferred to the isobutane stripper 21 through line 20 per hour. In the isobutane stripper 21, an isobutane fraction is separated and recycled through line 24 to the first alkylation reactor 5. The vessel employed as an isobutane stripper is a fractionating column containing the conventional trays, reboiling means, refluxing means and the like, all of which are well-known to the art. The product alkylate is recovered from the isobutane stripper as a bottoms fraction through line 22 at a rate of about 600 moles per hour. Normal butane is separated from the process through line 23 as a sidecut from the isobutane stripper 21, the n-butane being separated at a rate of about 50 moles per hour. The isobutane is taken as a sidecut from a higher tray and recycled to the first alkylation reactor 5 by way of lines 24 and 3 at a rate of about 3,320 moles per hour, the recycle stream further containing about 500 moles of n-butane and 225 moles of propane per hour attributable to imprecise fractionation in the isobutane stripper 21.

An overhead fraction is recovered from the isobutane stripper 21 and charged to a depropanizer column 26 through line 25. An overhead fraction charged through line 25 comprises about 100 moles of propane, 230 moles of isobutane and 25 moles of n-butane per hour. In the depropanizer column, the feed from line 25 is subjected to fractionation for the separation of propane. The bottoms fraction comprises about 25 moles of n-butane and about 230 moles of isobutane per hour, and this bottoms fraction is withdrawn through line 27 and transferred into line 24 for use in the recycle isobutane stream. Propane, admixed with some hydrofluoric acid, is recovered overhead from the depropanizer column 26 through line 28 at a rate of about 100 moles per hour, and the overhead stream passes through line 28 into line 29 in admixture with hydrofluoric acid from line 30. The propane-hydrofluoric acid mixture is passed through a condenser 31, and the resulting liquefied mixture is continued through line 32 into a settler 33. Most of the hydrofluoric acid settles out as a lower liquid phase of relatively pure acid, and is withdrawn from the settler 33 through line 34. This relatively highly concentrated hydrofluoric acid may be recovered or recycled to line 10 or line 17 for use in alkylation reactor 5 and/or 11. The upper liquid propane phase is withdrawn from the settler 33 by way of line 35 and transferred to a hydrofluoric acid stripper 36 wherein any residual hydrofluoric acid is separated and recovered overhead through line 30 to be further treated as heretofore described. The propane is recovered from the hydrofluoric acid stripper 36, and from the alkylation process, through line 37 at a rate of about 100 moles per hour.

The foregoing description illustrates some of the advantages of the present invention when embodied in a hydrofluoric acid-catalyzed isoparaffin-olefin alkylation process. In keeping with the prior art dual-reactor system, reaction conditions in the first alkylation reactor 5 and the second alkylation reactor 11 include a desirable and high isobutane/olefin mole ratio of about 13:1 which is conducive to improved alkylate product quality. Yet fractionation requirements in the isobutane stripper 21 need only be sufficient to separate isobutane equivalent to an overall isobutane/olefin mole ratio of less than about 7:1. Thus, the alkylate product quality is equal or superior to alkylate produced by the more conventional alkylation processes, while the fractionation requirements are substantially reduced with attendant savings in capital and utilities cost. By contrast, alkylate produced in conventional hydrofluoric acid-catalyzed alkylation processes using an overall isobutane/olefin mole ratio of about 7:1 would be of relatively low quality and lack utility as a blending stock to upgrade low octane gasoline stocks to a desired octane level. The alkylation process of the present invention embodies the improvements and advantages of the prior art process, and offers a further savings in capital and utilities cost attributable to improved hydrofluoric acid circulation and a reduction in the hydrofluoric acid inventory of the process.

Other advantages are to be derived from the practice of this invention. For example, in the course of the alkylation process, the hydrofluoric acid catalyst tends to become diluted with certain organic materials which are largely polymeric by-products of the alkylation reaction. This necessitates at least periodic regeneration of the acid catalyst to maintain a desired acid concentration. It has been observed that the second alkylation reactor of a dual reactor system produces a lesser amount of said organic material than does the first reactor. In any case, those prior art processes employing a dual reactor system, each of which embodies an independent acid catalyst recycle system in an otherwise interacting alkylation system, experience undue difficulty in maintaining a desired acid concentration in each of said independent recycle systems. By processing the hydrofluoric acid in accordance with the present invention, this difficulty is substantially obviated.

The alkylation process of the present invention may be applied, in general, to the alkylation of $C_4$–$C_6$ isoparaffins. The preferred isoparaffins are isobutane and isopentane, particularly isobutane. A mixture of two or more isoparaffins may be employed if so desired. A suitable isoparaffin feedstock for use in the present process may contain some non-reactive contaminants such as normal paraffins. For example, a conventional commercial isobutane alkylation feedstock generally contains about 95 wt.% isobutane, 4 wt.% n-butane and about 1 wt.% propane.

Olefin-acting alkylating agents suitable for use herein include $C_3$–$C_6$ olefins, alkyl halides, alkyl sulfates, alkyl phosphates, alcohols, and the like. $C_3$–$C_5$ olefins and alkyl halides are preferred, particularly propylene, butylenes, amylenes, and mixtures thereof. The process of the present invention may be advantageously applied to the alkylation of an isoparaffinic hydrocarbon utilizing a mixture of two or more olefin-acting alkylating agents. For example, many conventional olefin feedstocks in commercial isoparaffin-olefin alkylation operations contain mixtures of propylene, butylenes and/or amylenes. Application of the present process to such mixtures will result in an improvement of the quality of the alkylate substantially equal to that obtained through the use of a single olefin. Similarly, a mixture of $C_3$–$C_5$ alkyl halides and olefins in any proportion is also suitably treated by the process of this invention. Typically, the $C_3$–$C_5$ olefin feedstocks are derived from petroleum refining processes, such as catalytic cracking, and may contain substantial amounts of saturated hydrocarbons, lighter and heavier olefins, etc. Such conventional olefin sources are suitable for use to provide the olefin-acting alkylating agent in the present process.

The alkylation catalyst employed herein is a hydrofluoric acid alkylation catalyst generally containing about 75 wt.% or more of titratable acid, about 5 wt.% or less of water, with organic diluent constituting the remainder. A particularly preferred catalyst comprises about 85 wt.% hydrofluoric acid and less than about 1 wt.% water.

In general, alkylation reaction conditions suitable for use in the present process, in which the isoparaffinic hydrocarbon is preferably isobutane, include a temperature of from about 0° to about 200° F., a contact time between the catalyst and reactants of from about 0.1 to about 30 minutes, and a pressure sufficient to maintain substantially liquid phase reaction conditions. A pressure differential of from about 5 to about 20 psig. is preferably maintained between the alkylation reaction zones to facilitate the transfer of hydrofluoric acid catalyst, and also the hydrocarbon effluent streams, as herein contemplated. In one preferred embodiment, a catalyst/hydrocarbon volume ratio of from about 0.1 to about 10 is employed, and the temperature is maintained at from about 90° to about 100° F.

The reaction mixture recovered from the alkylation reactors may be passed through a reaction mixture soaker as is commonly practiced, and it is intended that both the alkylation reactor and reaction mixture soaker be included within the scope of the term "alkylation reaction zone". Suitable reaction mixture soakers are well known in the art. For example, the reaction mixture soakers described in U.S. Pat. No. 3,560,587 and U.S. Pat. No. 3,607,970 may suitably be employed in the present process. Such reaction mixture soakers are typically vessels equipped with perforated trays, baffle sections, or the like, to maintain the reaction mixture of catalyst and hydrocarbons charged from the alkylation reactor as a fairly homogeneous mixture or emulsion for a predetermined length of time. The mixture of catalyst and hydrocarbons is maintained in the reaction mixture soaker for a time which depends on the composition of the reaction mixture. A reaction mixture soaker residence time of from about 1 minute to about 30 minutes is preferred. The temperature and pressure maintained in the reaction mixture soaker are the same as the temperature and pressure maintained in the alkylation reactor.

Separation of the alkylation reaction mixture into a hydrocarbon phase and an acid catalyst phase is typically effected by allowing the alkylation reaction mixture effluent from the alkylation reactor or soaker to stand under quiescent conditions whereby the acid catalyst settles out from the hydrocarbon phase comprising the alkylate, isoparaffin and light hydrocarbon gases. The hydrocarbon phase is then easily mechanically separated from the acid catalyst phase. The temperature and pressure employed in such a settling operation are substantially the same as those described above in connection with the alkylation reaction conditions. The hydrocarbons and the catalyst are preferably maintained in the liquid phase during the separation operation.

Some means for withdrawing heat from the alkylation zone is necessary for operation of the process. A variety of means for accomplishing heat withdrawal is well known. For example, in a preferred embodiment, the heat generated in the alkylation reaction may be withdrawn directly from the alkylation reactor by indirect heat exchange between cooling water and the reaction mixture in the reactor.

The hydrocarbon effluent stream recovered from the first alkylation zone, by settling the reaction mixture to separate the catalyst, is combined with a second portion of the olefin-acting alkylating agent and charged to the second alkylation reactor, wherein the combined olefin and hydrocarbon effluent are contacted with the alkylation catalyst. It is contemplated that sufficient isoparaffin is charged to the first alkylation zone so that no further make-up isoparaffin, or isoparaffin recovered from fractionation, need be added to the hydrocarbons charged to the second reactor. Under some conditions, it may be advantageous to charge some further fresh isoparaffin to the second alkylation reactor, and such a modification is within the scope of the present process.

In general, the benefits and advantages of the present process are provided when the isoparaffinic reactant is charged into a series of at least two separate alkylation zones and contacted with at least two different portions of the olefin-acting alkylating agent. One obvious modification of the present process is to divide the olefin-acting alkylating agent into a plurality of portions, e.g., three or more. The isoparaffin and a first portion of the olefin-acting alkylating agent are contacted in a first alkylation zone and the hydrocarbons are separated from the first catalyst to form the hydrocarbon effluent stream. The hydrocarbon effluent from the first alkylation zone is then contacted with a second portion of the olefin-acting alkylating agent in the second alkylation zone. The hydrocarbon effluent recovered from the second alkylation zone is contacted with a third portion of the olefin-acting alkylating agent in a third alkylation zone, etc. The hydrocarbon effluent from the last alkylation zone in the series provides a reaction product stream which is fractionated to recover the alkylation reaction product and to separate the isoparaffin contained therein for recycle to the first alkylation zone.

In a preferred embodiment wherein the olefin-acting alkylating agent is divided into two portions, it is preferred that neither portion contain less than about 10 vol.% of the whole. For example, in a continuous operation, the first portion may be fed to the first alkylation reaction zone at a rate of about 10 moles per hour. The second portion being then fed to the second alkylation reaction zone at a rate of at least about 1 mole per hour and not in excess of about 100 moles per hour. Preferably, the two portions do not vary by more than from about 1:5 to about 5:1. Best results are achieved when the two portions contain roughly equimolar amounts of the olefin-acting alkylating agent. In this manner, the amount of isoparaffin required to provide an optimum molar excess in each alkylation reaction zone is miantained at a minimum, and the highest quality product can be produced in each of the alkylation reaction zones.

The alkylation reaction product produced in the preferred embodiment of the present process, when isobutane is employed as the isoparaffin, and propylene and butylenes are utilized as the olefin-acting alkylating agent, includes $C_5$–$C_8$ saturated hydrocarbons resulting from the alkylation reaction of the isoparaffin of the olefin-acting alkylating agent in both the first and second alkylation zones. The primary products include, for example, dimethylpentanes and trimethylpentanes. It is known that more highly branced hydrocarbons possess superior properties as motor fuel components, and the present invention is directed, in part, to providing an alkylation reaction product containing a higher ratio of more highly branched hydrocarbons, such as trimethylpentanes, to less branched hydrocarbons, such as dimethylhexanes. The foregoing is accomplished through the use of the series flow of isoparaffin and hydrofluoric acid catalyst to provide optimum alkylation conditions, including an extremely high mole ratio of isoparaffin to olefin in the alkylation reactors. It is thus apparent that the present invention provides a process for producing a superior motor fuel alkylate product by a method more economical and convenient than has been available in the prior art.

We claim as our invention:

1. A process for the alkylation of an isoparaffinic hydrocarbon with an olefin-acting alkylating agent which comprises:
   (a) commingling said isoparaffinic hydrocarbon and a first portion of said olefin-acting alkylating agent in a first alkylation reaction zone at alkylation reaction conditions and in contact with a hydrofluoric acid catalyst of at least 75 wt.% titratable acid and 5 wt.% or less water;
   (b) separating the hydrofluoric acid phase from the reaction effluent of said first alkylation reaction zone effluent and recovering a hydrocarbon phase comprising alkylate and unreacted isoparaffinic hydrocarbon;
   (c) commingling said hydrocarbon phase with a second portion of said olefin-acting alkylating agent in a second alkylation reaction zone at alkylation reaction conditions and in contact with said hydrofluoric acid phase separated from the effluent of said first alkylation reaction zone;
   (d) separating the acid phase from the reaction effluent of said second alkylation reaction zone, and recycling the same to said first alkylation reaction zone; and,
   (e) recovering the alkylation product from the hydrocarbon phase separated in step (d).

2. The process of claim 1 further characterized in that said isoparaffinic hydrocarbon is a $C_4$–$C_5$ isoparaffinic hydrocarbon.

3. The process of claim 1 further characterized in that said isoparaffinic hydrocarbon is isobutane.

4. The process of claim 1 further characterized in that said olefin-acting alkylating agent is a $C_3$–$C_5$ olefinic hydrocarbon.

5. The process of claim 1 further characterized in that said olefin-acting alkylating agent is a mixture of propylene and butylenes.

6. The process of claim 1 further characterized in that from about 20 to about 80 volume percent of the olefin-acting alkylating agent is commingled with said isoparaffinic hydrocarbon in said first alkylation reaction zone.

7. The process of claim 1 further characterized in that the alkylation reaction conditions in said first alkylation reaction zone and said second alkylation reaction zone include a pressure sufficient to maintain a substantially liquid phase reaction mixture and a pressure differential between said first and second alkylation reaction zones of from about 5 to about 20 psig.

* * * * *